United States Patent [19]

Reichl et al.

[11] 4,334,531
[45] Jun. 15, 1982

[54] INHALATOR

[75] Inventors: Ernst Reichl, Munich; Herbert Marloth, Siegertsbrunn, both of Fed. Rep. of Germany

[73] Assignee: Bosch-Siemens Hausgeräte GmbH, Munich, Fed. Rep. of Germany

[21] Appl. No.: 160,621

[22] Filed: Jun. 18, 1980

[30] Foreign Application Priority Data

Jun. 19, 1979 [DE] Fed. Rep. of Germany ... 7917568[U]

[51] Int. Cl.³ .............................................. A61M 11/00
[52] U.S. Cl. .......................... 128/200.14; 128/200.16; 239/102; 239/338; 261/DIG. 65
[58] Field of Search .............. 128/200.16, 200.17, 128/200.18, 200.19, 200.21, 200.22, 200.23, 203.15; 261/DIG. 65, 1; 239/102, 338, 380

[56] References Cited

U.S. PATENT DOCUMENTS

| | | | |
|---|---|---|---|
| 3,506,004 | 4/1970 | Mann et al. | 128/200.23 |
| 3,812,853 | 5/1974 | Crain | 128/200.17 |
| 4,119,096 | 10/1978 | Drews | 128/200.16 |
| 4,206,758 | 6/1980 | Hallworth et al. | 128/203.15 |

FOREIGN PATENT DOCUMENTS 4039 9/1979 European Pat. Off. ....... 128/200.16

Primary Examiner—Henry J. Recla
Attorney, Agent, or Firm—Herbert L. Lerner; Laurence A. Greenberg

[57] ABSTRACT

Inhalator, including a housing having a space formed therein which is accessible from outside the housing, a first fluid container having a pump and a second fluid container without a pump being selectably placeable in the space for emitting fluid, an atomizing element for receiving fluid emitted from the containers, a manually operable actuating element being slideable through a given region for turning the atomizing element on and off and for driving the pump of the first fluid container, and a fixed receptacle for selectably holding the first fluid container so it extends into the given region and for holding the second fluid container out of the given region.

3 Claims, 3 Drawing Figures

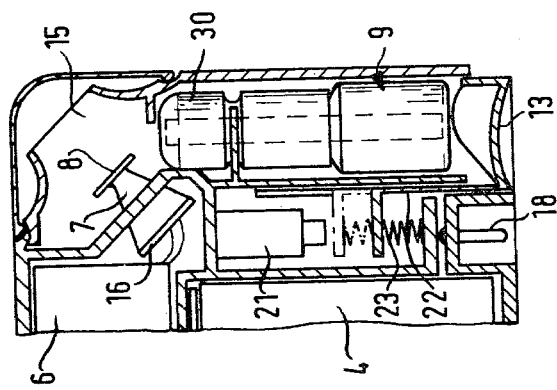
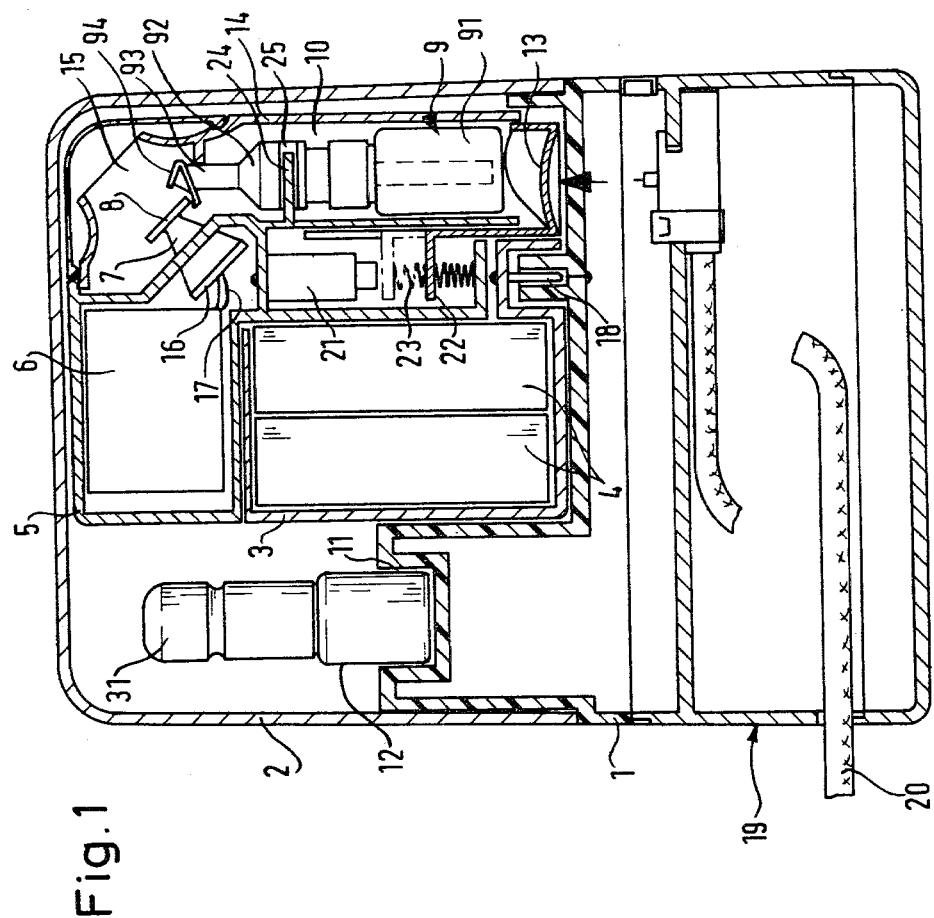

INHALATOR

The invention relates to an inhalator with an atomizing element which is preferably activated by ultrasonic flexural waves or vibration oscillations having a space which is accessible from the outside for holding a container with inhalation fluid and fluid admission means, and also with a manually operable actuating element for turning the atomizing element on and off.

Known inhalator devices of the above-mentioned type have a portable housing storage space in which only one fluid container with a small discharge opening can be placed and fastened. A wick, which serves for admitting the fluid, has one end thereof which extends into the interior of the fluid container, and another end which is in contact with the atomizing element. The liquid container is constructed so as to be large enough to contain inhalation-fluid for several inhalation treatments. An inhalator of this type serves for the care and treatment of the mouth and throat regions.

In other known inhalation devices which contain means for storing medicinally active substances for treating the breathing passages, for asthma sufferers, for example, the dosing of active liquid substance is effected through mechanical means by a release mechanism which activates a spray valve for a short time. In inhalators of this type, the very accurate metering or dosing of the active fluid is most essential.

However, just as important for the user, i.e. for the asthma sufferer, is the fact that the inhalator should be so dimensioned that he can carry it along with him at all times, to enable the device to be used immediately in the case of an asthma attack. Since regular use of the first-mentioned inhalator is required to provide for lasting results of the treatment, the user is inconvenienced by having to take both inhalation devices along when going on a trip.

It is accordingly an object of the present invention to provide an inhalator which overcomes the hereinafore-mentioned disadvantages of the heretofore-known devices of this general type, and to especially construct an inhalator of the first-mentioned type in such a manner that with a single device, preferably constructed in a pocket format, general inhalation treatments can be given, as well as special applications with exactly dosed medicinally active substances.

With the foregoing and other objects in view there is provided, in accordance with the invention, an inhalator comprising a housing having a space formed therein which is accessible from outside the housing, a first fluid container having a pump and a second fluid container without a pump being selectably placeable in the space for emitting fluid, an atomizing element for receiving fluid emitted from the containers, a manually operable actuating element being slideable through a given region for turning the atomizing element on and off and for driving the pump of the first fluid container, and a fixed receptacle for selectably holding the first fluid container so it extends into the given region and for holding the second fluid container out of the given region.

In accordance with an added feature of the invention, the receptacle is in the form of a fork having an open end, and the containers have grooves formed therein into which the fork is slideable.

In accordance with another feature of the invention, the housing has another space formed therein for accommodating the fluid container which is not disposed in the first-mentioned space. This gives the user the possibility of changing the inhalator for the desired application with little effort. For example, the asthma patient is able to change the inhalator in the morning, after the regular inhalation treatment, to the drug-application mode, so that he has the device ready in case of an asthma attack at all times.

With inhalation-fluids, the difficulty arises that the volatile compounds of the fluid evaporate from the fluid-container after storage for a longer period, and that in case of a medicinal substance, the substance deteriorates when exposed to the air. This difficulty is removed effectively, since in accordance with a further feature of the invention, there are provided caps for air-tightly sealing the fluid containers. The caps can be placed onto the ends where the fluids are discharged.

Other features which are considered as characteristic for the invention are set forth in the appended claims.

Although the invention is illustrated and described herein as embodied in an inhalator, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 1 is a diagrammatic cross-sectional view of the inhalator according to the invention, seated on a battery charger;

FIG. 3 is a fragmentary diagrammatic cross-sectional view of the inhalator according to FIG. 1, separated from the battery charger.

Figure 2:
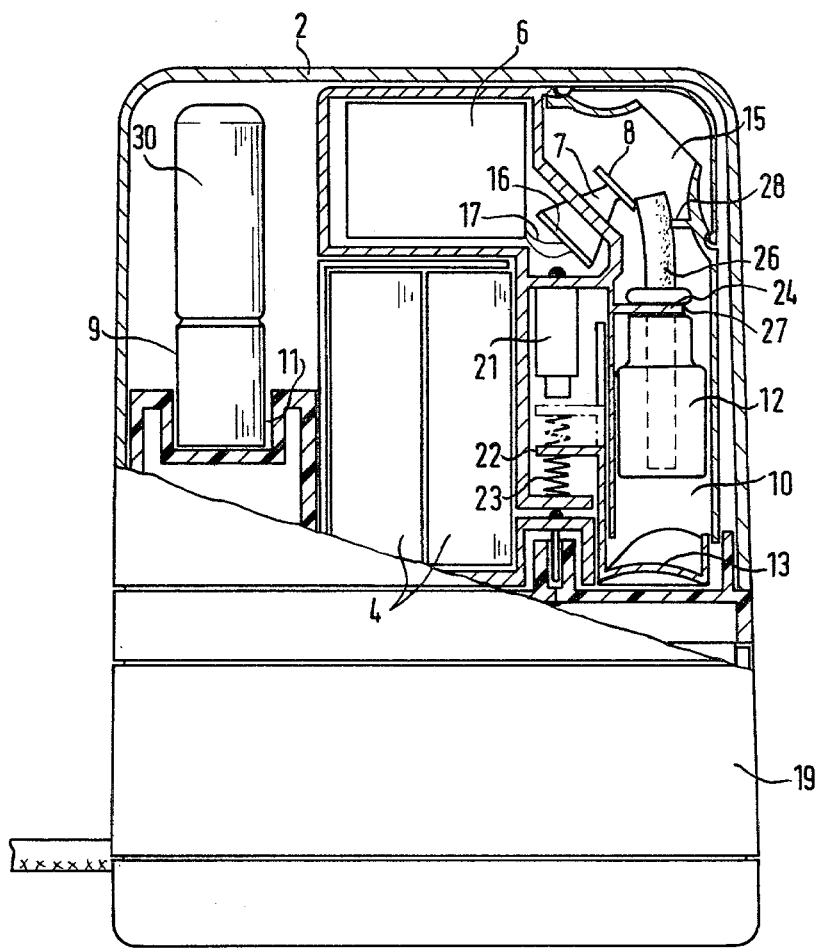
FIG. 2 is a diagrammatic elevational view, partly in cross section, of the inhalator according to FIG. 1, with a different container.

Referring now to the figures of the drawing and first particularly to FIG. 1 thereof, it is seen that the inhalator according thereto is constructed as a portable or pocket device. It comprises the following basic parts:

A plastic housing 1 with a cap 2 which can be placed thereupon, a battery set 4 contained in part 3 of the housing, an electronic vibration generator 6 which is disposed in an upper chamber 5 of the housing 1 having an atomizing element 7 with an atomizing plate 8 connected therewith, a storage space 10 in which a first liquid container 9 is located, another space 11 for storage of a second liquid container 12, and also an actuating element 13 in the form of a pressure key which can be operated manually such as through a non-illustrated hole formed in the housing 1 or by an actuator attached to the element 13. In order to use the inhalator the cap 2 must be removed. Under the cap 2 there is a likewise removable cover 14 which is provided with an atomizing opening 15. The atomizing element 7 comprises a conical sound transducer which carries a piezo-ceramic layer 16 on one side thereof, and the atomizing-plate 8 on the other side thereof. The atomizing element 7 is in electrical connection with the electronic vibration generator 6 through the electric lines 17, so that ultrasonic vibrations are transmitted from the vibration generator 6 to the atomizing element 7. For operating the vibration generator, there are provided the batteries 4 and an accumulator, which can be connected to a battery charger 19 by means of the contact 18 by placing the inhalator onto the battery charger 19. The battery charger 19 which is only diagrammatically shown is connected through the electric line 20 to a conventional current network. The vibration generator 6 can be switched-on by the actuating element 13 through switching means 21. A slide 22 which is part of the housing 1 is movable in the direction of the arrow, and has a slightly inwardly curved pressure surface formed on the actuating element 13 which is a part of the slide 22. The actuating element 13 and therefore also the slide 22 can be moved upward in the direction of the arrow into the dot-dash phantom position against the force of a spring 23, so that the angular projection of the slide 22 serves as seat for the spring 23 and for operating the slide 22. In the region of the actuating element 13, the slide 22 in conjunction with the surrounding walls of the housing form the storage space 10 for receiving the first fluid container 9. This space can be closed off by the hereinafore-mentioned cover 14 after the liquid container 9 has been inserted. In the space 10, a fixed open fork-shaped push-in container-receptacle 24 is provided. The fluid container 9 which has a corresponding groove 25 can be inserted into the receptacle 24, and thereby secured in a predetermined position with respect to the atomizer plate 8. The first fluid container which is designated with reference numeral 9 serves for storing a liquid medicinal agent for the treatment of asthma-sufferers.

Without describing unnecessary details, the liquid container 9 essentially comprises two parts, i.e. a lower part 91, and an upper part 92. The lower part 91 is slideable against a spring force with respect to the upper part 92. The upper part 92 has a cylindrical projection 93 of lesser diameter, which is perforated by a discharge duct with an upper discharge orifice. At the free end of the projection 93 and in the region of the discharge opening there is disposed a make-ready or supply device in form of a dish 94 which is open toward the atomizing element 8. The concave dish which is open toward the top is partly covered by a reflection shield which is inclined toward the atomizing element 8. Inside the fluid container 9, there is provided a non-illustrated conventional displacement-transporting mechanism such as a pump for liquids with a one-way valve, for example, which can be operated by compressing or pressing together the two cylindrical parts 91 and 92. Furthermore, the space in the fluid container which is not taken up by the liquid can be filled with a gas which is continuously kept above atmospheric pressure. For operation of the inhalator the cap 2 is removed, and the user presses his thumb on the actuating element 13, so that the switch 21 is first operated, and thereby the vibration generator 6 and the atomizing element 7 are set in operation. Then, after further motion of the slide 22, the means for transporting the fluid, i.e. the lower, slideable part 91 of the fluid container and the displacement transporting mechanism contained therein are operated. This causes an exactly-dosed amount of fluid, corresponding to the stroke of the pump, to flow into the dish 94, whereby the reflection shield reflects the liquid jet onto the dish. There the transported amount of the fluid comes in contact with the atomizing element 8, and is discharged to the outside in the form of a fluid-mist through the atomizing opening 15, into the breathing passages of the asthma patient.

As shown in FIG. 2, the fluid container designated with reference numeral 12 is provided with a wick 26, as the liquid-feeding device, which extends above the fluid container 12, and is in contact with the inhalation-fluid in the container. This fluid container 12 also has a groove 27, through which it can be fitted and secured on the container-receptacle 24 in the storage space 10. The free end of the wick 26 is pressed against the atomizing element 8 by a rib 28. As the figures show, the fluid container 12 is considerably shorter than the fluid container designated with reference numeral 9 in FIG. 1, because in the first-mentioned fluid container no pumping system need be provided. The space 10 is so dimensioned that it can either accomodate the fluid container 9 or the fluid container 12, as desired. If the inhalator is used according to FIG. 2, only the vibration generator 6 is activated by operating the actuating element 13, while when it is used according to FIG. 1 a pumping operation is also performed by the continued motion of the actuating element 13. As shown in FIGS. 1 and 2, the fluid container 12 or 9, respectively, which is not used is securely stored in the additional storage space 11, where it is in readiness for changing the inhalator to the other fluid. It is also shown in the figures that both fluid containers 9 and 12 can be sealed for fluids and airtightly closed by the caps 30 and 31, respectively, which can be placed on the fluid discharge ends of the containers. As shown in FIG. 3, it is also possible to close the fluid container in the space 10 (the container 9 being shown in FIG. 3), by using its respective cap.

We claim:

1. An inhalator comprising a housing having a lower portion and a removable cap portion mounted on said lower portion thereby defining a space therein, wall means in said space defining a compartment, said compartment having an outlet opening, a cover removably mounted over said outlet opening wherein said cap and cover are removable to allow access into said space and compartment from outside said housing, a first fluid container having an outlet and pump means for pumping fluid from said outlet of said first fluid container when said pump means and first fluid container are compressed, a second fluid container having an outlet with means for emitting fluid from said outlet mounted therein, said second fluid container having a length shorter than the length of said first fluid container, receptacle means mounted in said compartment for removably receiving and holding one of said containers such that the outlet of said respective container is adjacent said outlet opening of said compartment, electrically operated atomizing means mounted in said compartment adjacent said outlet of one of said fluid containers for receiving and atomizing fluid emitted from the outlet of one of said containers, electrical source means mounted in said space, a switch mounted in said compartment and electrically connected between said electrical source means and said atomizing means, holding means mounted in said space for receiving and storing one of said containers, said first and second fluid containers being removably and interchangeably mounted between said receptacle means and said holding means, manually operable actuating means slidably mounted in said compartment and operable, when said first fluid container is mounted in said receptacle means, for simultaneously actuating said switch for turning said atomizing means on and off and for impinging upon said first fluid container for driving said pump means and pumping fluid from said first fluid container toward said atomizing means, and operable, when said second fluid container is mounted in said receptacle means, for solely actuating said switch for turning said atomizing means on and off as fluid is transferred to said atomizing means from said fluid emitting means, whereby one of said containers is mounted in said receptacle means for use while the other is mounted in said holding means for storage.

2. Inhalator according to claim 1, wherein said receptacle means is in the form of a fork having an open end, and said containers have grooves formed therein into which said fork is slideable for fixing said container in place, said first fluid container being compressible between said fork and said actuating element upon manual operation for actuating said pump.

3. Inhalator according to claim 1, including caps removably mounted on said fluid containers for airtightly sealing said fluid containers.

* * * * *